United States Patent

Hoffmann et al.

[11] 4,119,715
[45] Oct. 10, 1978

[54] PESTICIDALLY ACTIVE O-(1-FLUORO-2-HALOGENO-ETHYL)-THIONOPHOSPHORIC (PHOSPHONIC) ACID ESTERS

[75] Inventors: Hellmut Hoffmann, Wuppertal; Dieter Arlt, Cologne; Bernhard Homeyer, Leverkusen; Ingeborg Hammann, Cologne, all of Germany

[73] Assignee: Bayer Aktiengesellschaft, Leverkusen, Germany

[21] Appl. No.: 808,227

[22] Filed: Jun. 20, 1977

[30] Foreign Application Priority Data

Jul. 7, 1976 [DE] Fed. Rep. of Germany ....... 2630561

[51] Int. Cl.$^2$ .................. A01N 9/36; C07F 9/165; C07F 9/40
[52] U.S. Cl. .................................. 424/216; 260/949; 260/954; 260/961; 260/963; 424/218; 424/222; 424/225
[58] Field of Search ............... 260/961, 963, 949, 954; 424/216, 218, 222, 225

[56] References Cited

U.S. PATENT DOCUMENTS

| 3,093,536 | 6/1963 | Loeffler | 260/961 X |
| 3,980,738 | 9/1976 | Arlt et al. | 260/963 X |

*Primary Examiner*—Anton H. Sutto
*Attorney, Agent, or Firm*—Burgess, Dinklage & Sprung

[57] ABSTRACT

O-(1-Fluoro-2-halogeno-ethyl)-thionophosphoric (phosphonic) acid esters of the formula

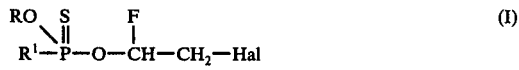

(I)

in which
R is alkyl, phenyl or phenyl carrying at least one substituent selected from the group consisting of halogen, alkyl, alkylthio and nitro,
R$^1$ is alkyl or alkoxy, and
Hal is halogen,
which possess arthropodicidal and nematicidal properties.

9 Claims, No Drawings

PESTICIDALLY ACTIVE O-(1-FLUORO-2-HALOGENO-ETHYL)-THIONO-PHOSPHORIC (PHOSPHONIC) ACID ESTERS

The present invention relates to and has for its objects the provision of particular new O-(1-fluoro-2-halogeno-ethyl)-thionophosphoric (phosphonic) acid esters which possess arthropodicidal and nematicidal properties, active compositions in the form of mixtures of such compounds with solid and liquid dispersible carrier vehicles, and methods for producing such compounds and for using such compounds in a new way especially for combating pests, e.g. arthropods and nematodes, with other and further objects becoming apparent from a study of the within specification and accompanying examples.

It is known from U.S. Pat. Nos. 2,701,225, 2,947,773 and 3,453,348 that chlorine-substituted alkylphosphoric (phosphonic) acid esters, for example O,O-diethyl-O-(1,2-dichlorethyl)-phosphoric acid ester (Compound A) and O,O-dimethyl-1-hydroxy-2,2,2-trichloroethane-phosphonic acid ester (Compound B), possess insecticidal and acaricidal properties.

The present invention now provides, as new compounds, the 1-fluoro-2-halogeno-ethyl-thionophosphoric (phosphonic) acid esters of the general formula

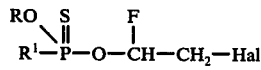

(I)

in which
R is alkyl, phenyl or phenyl carrying at least one substituent selected from the group consisting of halogen, alkyl, alkylthio and nitro,
R$^1$ is alkyl or alkoxy, and
Hal is halogen.

Preferably, R represents straight-chain or branched alkyl with 1 to 3 carbon atoms, phenyl, chlorophenyl, nitrophenyl, alkylphenyl or alkyl-alkylthio-phenyl with 1 to 3 carbon atoms per alkyl or alkylthio radical, R$^1$ represents straight-chain or branched alkyl or alkoxy with 1 to 3 carbon atoms, and Hal represents chlorine or bromine.

Surprisingly, the 1-fluoro-2-halogeno-ethyl-thionophosphoric (phosphonic) acid esters according to the invention have a better insecticidal, acaricidal and nematicidal action than the chlorine-substituted alkylphosphoric (phosphonic) acid esters of analogous structure, and of the same type of action, which are known from the literature. The compounds according to the present invention thus represent a genuine enrichment of the art.

The present invention also provides a process for the preparation of a 1-fluoro-2-halogeno-ethyl-thionophosphoric (phosphonic) acid ester of the formula (I) in which (a), in the case where R$^1$ denotes alkyl, an O-(1-fluoro-2-halogeno-ethyl)-thionoalkanephosphonic acid ester halide of the general formula

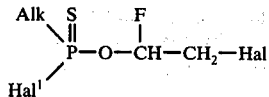

(II), in which

Hal has the above-mentioned meaning,
Alk denotes alkyl and
Hal$^1$ represents halogen, preferably chlorine,
is reacted with an alcohol or phenol of the general formula

R—OH (III), in which R has the above-mentioned meaning, the latter being employed either as such in the presence of an acid acceptor, or in the form of an alkali metal salt or alkaline earth metal salt, (b), in the case where R$^1$ denotes alkoxy, an O-(1-fluoro-2-halogeno-ethyl)-thionophosphoric acid ester dihalide of the general formula

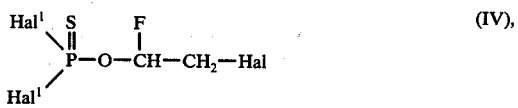

(IV), in which Hal and Hal$^1$ have the above-mentioned meanings, is reacted with an alcohol of the general formula

R$^2$OH (V), in which R$^2$ denotes alkyl, preferably straight-chain or branched alkyl with 1 to 3 carbon atoms, the latter being employed either as such in the presence of an acid acceptor or in the form of an alkali metal salt or alkaline earth metal salt thereof, to give an O-alkyl-O-(1-fluoro-2-halogeno-ethyl)-thionophosphoric acid diester halide of the general formula

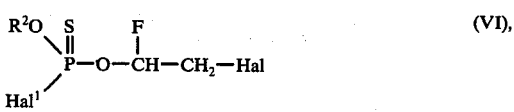

(VI), in which R$^2$, Hal and Hal$^1$ have the above-mentioned meanings, which is then reacted, if appropriate in the presence of a solvent, with an alcohol or phenol of the general formula (III) either as such in the presence of an acid acceptor or in the form of an alkali metal salt or alkaline earth metal salt thereof.

If, for example, O-(1-fluoro-2-chloroethyl)-thiono-n-propanephosphonic acid ester chloride and 4-methylthiophenol or O-(1-fluoro-2-chloro-ethyl)-thionophosphoric acid ester dichloride, methanol and 4-ethylphenol are used as starting materials, the course of the reaction can be represented by the following equations:

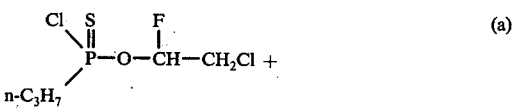

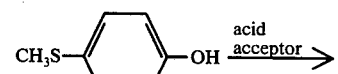

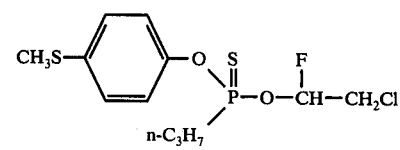

(a)

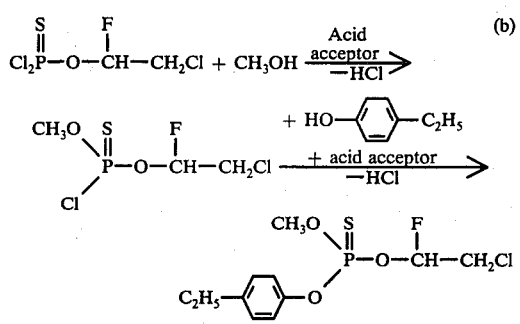

(b)

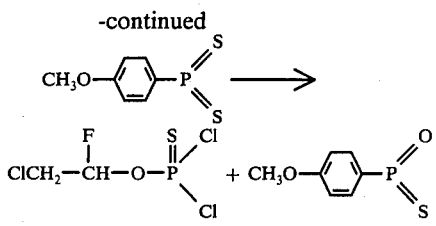

The alcohols (V), and alcohols or phenols (III) to be used as starting materials are known and can be prepared in accordance with generally customary processes described in the literature, even on a large industrial scale.

The following may be mentioned as individual examples of the starting materials: methanol, ethanol, n- and isopropanol, phenol, 2-, 3- and 4-chlorophenol, 2,4- and 2,6-dichlorophenol, 2,4,5- and 2,4,6-trichlorophenol, pentachlorophenol, 2-, 3- and 4-nitrophenol, 2,4-dinitrophenol, 2-, 3- and 4-methylphenol, 2,3-, 2,4- and 3,4-dimethylphenol, 4-ethylphenol, 2,6-diethylphenol, 2-isopropylphenol, 3-ethyl-5-methylphenol, 2-isopropyl-5-methylphenol and 3-methyl-4-methylthiophenol.

The O-(1-fluoro-2-halogeno-ethyl)-thionophosphoric (phosphonic) acid ester halides (II) and (IV), which are also to be used as starting compounds, are new.

They are obtained by reacting O-(1-fluoro-2-halogeno-ethyl)-phosphoric (phosphonic) acid ester halides of the general formula

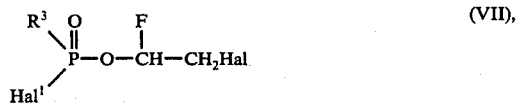

in which
Hal and Hal¹ have the above-mentioned meanings and R³ represents alkyl or Hal¹,
with alkane dithiophosphonic acid anhydrides or aryldithiophosphonic acid anhydrides of the general formula

in which R⁴ represents lower alkyl or aryl, if appropriate in the presence of phosphorus sulphochloride and, if appropriate, in the presence of an organic solvent.

If, for example, O-(1-fluoro-2-chloro-ethyl)-phosphoric acid ester dichloride and anisyldithiophosphonic acid anhydride are used as starting materials, the course of the reaction can be represented by the following equation:

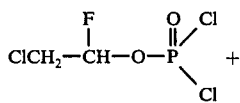

-continued

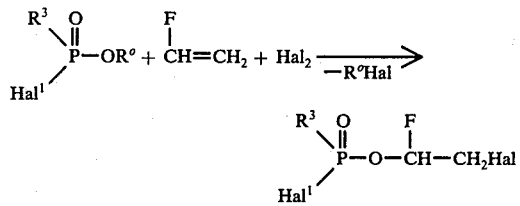

Preferably, in these formulae (VII) and (VIII), R³ denotes chlorine or straight-chain or branched alkyl with 1 to 3 carbon atoms and R⁴ denotes straight-chain or branched alkyl with 1 to 4 carbon atoms or phenyl which is optionally substituted by lower alkyl or lower alkoxy.

The dithiophosphonic acid anhydrides (VIII) are described in the literature. The following may be mentioned as individual examples: methane-, ethane-, n-propane-, isopropane-, phenyl- and (4-methoxyphenyl)-dithiophosphonic acid anhydride.

The O-(1-fluoro-2-halogenoethyl)-phosphoric (phosphonic) acid ester halides (VII) may be prepared, from the corresponding halogenated phosphoric (phosphonic) acid esters and vinyl fluoride, with simultaneous use of haloginating agents, such as chlorine or bromine, in accordance with the following equation:

$$\underset{Hal^1}{\overset{R^3}{\diagdown}}\!\!\!\overset{O}{\underset{}{\overset{\|}{P}}}\!\!-OR^o + \overset{F}{\underset{}{\overset{|}{CH}}}\!=CH_2 + Hal_2 \xrightarrow{-R^oHal}$$

$$\underset{Hal^1}{\overset{R^3}{\diagdown}}\!\!\!\overset{O}{\underset{}{\overset{\|}{P}}}\!\!-O-\overset{F}{\underset{}{\overset{|}{CH}}}\!-CH_2Hal$$

wherein
R³, Hal and Hal¹ have the above-mentioned meanings and
R° represents lower alkyl.

The following may be mentioned as individual examples of the O-(1-fluoro-2-halogeno-ethyl)-phosphoric (phosphonic) acid ester halides (VII): O-(1-fluoro-2-chloromethyl)- and O-(1-fluoro-2-bromoethyl)-phosphoric acid ester dichloride, and O-(1-fluoro-2-chloroethyl)- or O-(1-fluoro-2-bromoethyl)-methane-, ethane-, n-propane- and isopropane-phosphonic acid ester chloride.

The process for the preparation of the compounds of the formula (II) or (IV) is preferably carried out in the presence of a suitable solvent or diluent. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride or chlorobenzene; ethers, for example diethyl ether, dibutyl ether and dioxane, ketones, for example acetone, methyl ethyl ketone, methyl isopropyl ketone and methyl isobutyl ketone; and nitriles, such as acetonitrile and propionitrile.

The reaction temperature can be varied within a fairly wide range. In general, the reaction is carried out at from 90° to 200° C., preferably at from 100° to 160° C.

The reaction is in general allowed to take place under normal pressure.

To carry out the process, the starting materials are in most cases employed in equimolar amounts. An excess of one or other reactant produces no significant advantages. The mixture is heated for several hours to the stated temperatures. The reaction mixture is cooled, an organic solvent, for example ligroin, is then added, and the organic phase is worked up in the usual manner by washing, drying and distilling off the solvent. The compounds are obtained in the form of distillable liquids and are characterized by their boiling point.

The following may be mentioned as individual examples of the O-(1-fluoro-2-halogeno-ethyl)-thionoalkane-phosphonic acid halides (II) and O-(1-fluoro-2-halogeno-ethyl)-thionophosphoric acid ester dihalides (IV): O-(1-fluoro-2-chloro- or -2-bromo-ethyl)-thionomethane-, ethane-, n-propane- and isopropane-phosphonic acid ester chloride and O-(1-fluoro-2-chloro- or 2-bromo-ethyl)-thionophosphoric acid ester dichloride.

The O-alkyl-O-(1-fluoro-2-halogeno-ethyl)-thionophosphoric acid diester halides (VI) also to be used as starting compounds are also new compounds, but can be prepared in accordance with generally customary processes from the corresponding dihalides (IV) by reaction with alcohols. The following may be mentioned as individual examples of these compounds: O-methyl-, O-ethyl-, O-n-propyl- and O-isopropyl-O-(1-fluoro-2-chloro- or -2-bromoethyl)-thionophosphoric acid diester chloride.

The process for the preparation of the compounds (I) according to the invention is preferably carried out in the presence of a suitable solvent or diluent. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; nitriles, such as acetonitrile and propionitrile.

All customary acid-binding agents can be used as acid acceptors. Alkali metal carbonates, such as sodium carbonate and potassium carbonate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at from 0° to 100° C., preferably at from 10° to 40° C.

In general, the reaction is allowed to take place under normal pressure.

To carry out process variant (a), the starting materials are preferably employed in equimolar amounts. An excess of one or other reactant produces no significant advantage. In general, the reactants are combined in one of the stated solvents, in the presence of an acid acceptor, and are stirred in most cases at an elevated temperature for several hours to complete the reaction. The reaction mixture is then worked up in the usual manner by washing with water, drying and distilling off the solvent.

To carry out process variant (b), it is preferred to add the solution of the alcohol (V) dropwise, while cooling, to the thionophosphoric acid dihalide (IV), stir the mixture for a short time thereafter, wash and dry it and distil off the solvent, after which the substance obtained is immediately reacted, in the second reaction stage, with an equimolar amount of the alcohol or phenol (III) in the presence of an acid acceptor. After stirring for several hours, the reaction mixture is cooled and the batch is poured into water and extracted by shaking with an organic solvent, for example methylene chloride. The organic phase is worked up in the usual manner by washing, drying and then distilling off the solvent. If the alcohol component is identical in the first and second stage, the dihalide (IV) is reacted with the alcohol — preferably in the form of an alkali metal salt or alkaline earth metal salt thereof — in the molar ratio of 1:2 and thereafter the working-up procedure described above is followed.

The new compounds are often obtained in the form of oils which in most cases cannot be distilled without decomposition but which can be freed from the last volatile constituents by so-called "slight distillation", that is to say by prolonged heating under reduced pressure to moderately elevated temperatures, and can be purified in this way. They are characterized by the refractive index.

As already mentioned, the 1-fluoro-2-halogeno-ethyl-thionophosphoric (phosphonic) acid esters according to the invention are distinguished by an excellent insecticidal, acaricidal and nematicidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The active compounds are well tolerated by plants, have a favorable level of toxicity to warm-blooded animals, and can be used for combating arthropod pests, especially insects and arachnids, and nematodes which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.; from the class of the Symphyla, for example *Scutigerella immaculata;* from the order of the Thysanura, for example *Lepisma saccharina;* from the order of Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.; from the order of the Anoplura, for example *Phylloxera vastatrix,* Pemphigus spp., *Pediculus humanus corporis,* Haematopinus spp. and Linognathus spp.; from the order of the Mallophaga, for example Trichodectes spp. and Damalinea spp.; from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.; from the order of the Homoptera, for example *Aleurodes brassicae, Bemisia tabaci, Trialeurodes vaporariorum,Aphis gossypii, Brevicoryne brassicae, Cryptomyzus ribis, Doralis fabae, Doralis* pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp. and Psylla spp.; from the order of the Lepidoptera, for example Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana, Clysia ambiguella, Homona magnanima and Tortrix viridana; from the order of the Coleoptera, for example Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis and Costelytra zealandica; from the order of the Hymenoptera, for example Diprion spp., Hoplocampa spp., Lasius spp., Monomorium pharaonis and Vespa spp.; from the order of the Diptera, for example Aëdes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia Bibio hortulanus, Oscinella frit, Phorbia spp., Pegomyia hyoscyami, Ceratitis capitata, Dacus oleae and Tipula paludosa, from the order of the Siphonaptera, for example Xenopsylla cheopis and Ceratophyllus spp., from the class of the Arachnida, for example Scorpio maurus and Latrodectus mactans; from the order of the Acarina, for example Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp., and Tetranychus spp..

The plant-parasitic nematodes include Pratylenchus spp., Radopholus similis, Ditylenchus dipsaci, Tylenchulus semipenetrans, Heterodera spp., Meloidogyne spp., Aphelenchoides spp., Longidorus spp., Xiphinema spp. and Trichodorus spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichlorofluoromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other insecticides, acaricides and nematicides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. insects, acarids and nematodes which comprises applying to at least one of correspondingly (a) such insects, (b) such acarids, (c) such nematodes, (d) the corresponding habitat thereof, i.e. the locus to be protected, e.g. to a growing crop, to an area where a crop is to be grown or to a domestic animal, a correspondingly combative or toxic amount, i.e. an insecticidally, acaricidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all the test insects had been killed and was 0% if exactly as many test insects were still alive as in the case of the untreated control.

The active compounds, amounts used and results can be seen from the table which follows:

Table 1

| Active compound | Degree of destruction in % at an active compound concentration of 5 ppm |
|---|---|
| Cl—CH$_2$—CH(Cl)—O—P(=O)(OC$_2$H$_5$)$_2$ (known) (A) | 0 |
| Cl—CH$_2$—CH(F)—O—P(=S)(OCH$_3$)$_2$ (3) | 100 |
| Cl—CH$_2$—CH(F)—O—P(=S)(OC$_2$H$_5$)$_2$ (4) | 100 |

Table 1-continued (*Tenebrio molitor* larvae in the soil)

| Active compound | Degree of destruction in % at an active compound concentration of 5 ppm |
|---|---|
| Cl—CH$_2$—CH(F)—O—P(=S)(OC$_2$H$_5$)—O—C$_6$H$_4$—NO$_2$ (6) | 100 |
| Cl—CH$_2$—CH(F)—O—P(=S)(OCH$_3$)—C$_2$H$_5$ (1) | 100 |

EXAMPLE 2

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (= mg/l), was decisive. The soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation had been completely avoided; it was 0% when the infestation was exactly the same as in the case of the control plants in untreated soil which had been infested in the same manner.

The active compound, the amounts applied and the results can be seen from the following table:

Table 2

(*Meloidogyne incognita*)

| Active compound | Degree of destruction in % at an active compound concentration of 20 ppm |
|---|---|
| Cl—CH$_2$—CH(Cl)—O—P(=O)(OC$_2$H$_5$)$_2$ (known) | 0 |
| Cl—CH$_2$—CH(F)—O—P(=S)(OC$_2$H$_5$)—O—C$_6$H$_3$(CH$_3$)—S—CH$_3$ (A) (2) | 100 |

Table 2-continued (*Meloidogyne incognita*)

| Active compound | Degree of destruction in % at an active compound concentration of 20 ppm |
|---|---|
| Cl—CH$_2$—CH(F)—O—P(=S)(OC$_2$H$_5$)—O—C$_6$H$_4$—NO$_2$ (6) | 100 |
| Cl—CH$_2$—CH(F)—O—P(=S)(OC$_2$H$_5$)—O—C$_6$H$_2$Cl$_3$ (7) | 100 |
| Cl—CH$_2$—CH(F)—O—P(=S)(OCH$_3$)—C$_2$H$_5$ (1) | 100 |

EXAMPLE 3

Test insect: *Phorbia antiqua* maggot in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all the test insects had been killed and was 0% if exactly as many test insects were still alive as in the case of the untreated control.

The active compounds, amounts used and results can be seen from the table which follows:

Table 3

(*Phorbia antiqua* maggot in the soil)

| Active compound | Degree of destruction in % at an active compound concentration of 5 ppm |
|---|---|
| Cl—CH$_2$—CH(Cl)—O—P(=O)(OC$_2$H$_5$)$_2$ | 0 |

Table 3-continued (*Phorbia antiqua* maggot in the soil)

| Active compound | | Degree of destruction in % at an active compound concentration of 5 ppm |
|---|---|---|
| (known) | (A) | |
| Cl—CH₂—CH(F)—O—P(=S)(OCH₃)(OCH₃) | | 100 |
| | (3) | |
| Cl—CH₂—CH(F)—O—P(=S)(OC₂H₅)(OC₂H₅) | | 100 |
| | (4) | |
| Cl—CH₂—CH(F)—O—P(=S)(OC₂H₅)—O—C₆H₃(CH₃)(S—CH₃) | | 100 |
| | (2) | |
| Cl—CH₂—CH(F)—O—P(=S)(OCH₃)(C₂H₅) | | 100 |
| | (1) | |
| Cl—CH₂—CH(F)—O—P(=S)(OC₂H₅)—O—C₆H₄—NO₂ | | 100 |
| | (6) | |

EXAMPLE 4

Myzus test (contact action)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% meant that all the aphids were killed whereas 0% meant that none of the aphids were killed.

The active compounds, the concentrations of the active compounds, the evaluation times and the results can be seen from the following table:

Table 4

(*Myzus* Test)

| Active compound | Active compound concentration in % | Degree of destruction in % after 1 day |
|---|---|---|
| (CH₃O)₂P(=O)—CH(OH)—CCl₃ (known) (B) | 0.1 | 50 |
| | 0.01 | 0 |
| Cl—CH₂—CH(Cl)—O—P(=O)(OC₂H₅)(OC₂H₅) (known) (A) | 0.1 | 100 |
| | 0.01 | 90 |
| | 0.001 | 0 |
| Cl—CH₂—CH(F)—O—P(=S)(OC₂H₅)—O—C₆H₄—NO₂ (6) | 0.1 | 100 |
| | 0.01 | 100 |
| | 0.001 | 100 |

EXAMPLE 5

Tetranychus test (resistant)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent and the stated amount of emulsifier and the concentrate was diluted with water to the desired concentration.

Bean plants (Phaseolus vulgaris) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all the spider mites were killed whereas 0% meant that none of the spider mites were killed.

The active compounds, the concentrations of the active compounds, the evaluation times and the results can be seen from the following table:

Table 5

(*Tetranychus* Test)

| Active compound | Active compound concentration in % | Degree of destruction in % after 2 days |
|---|---|---|
| (CH₃O)₂P(=O)—CH(OH)—CCl₃ (known) (B) | 0.1 | 0 |
| Cl—CH₂—CH(F)—O—P(=S)(OC₂H₅)—O—C₆H₃(CH₃)(S—CH₃) (2) | 0.1 | 98 |

The process of the present invention is illustrated by the following preparative examples:

EXAMPLE 6

(a)
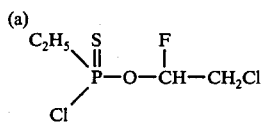

A slurry of 150 ml of toluene, 96 g (0.4 mol) of anisyl-dithiophosphonic acid anhydride and 84 g (0.4 mol) of O-(1-fluoro-2-chloro-ethyl)-ethane-phosphonic acid ester chloride was heated for 2 hours to 115°-120° C., cooled and poured into 1 l of ligroin. The mixture was filtered over kieselguhr, the solvent was evaporated off and the residue was distilled. 33 g (73% of theory) of O-(1-fluoro-2-chloro-ethyl)-thionoethanephosphonic acid ester chloride of boiling point 82° C./2 mm Hg were obtained.

(b)                                      (1)
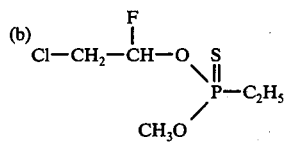

A mixture of 3.5 g of methanol and 11 g of triethylamine was added to a mixture of 100 ml of toluene and 23 g (0.1 mole) of O-(1-fluoro-2-chloro-ethyl)-thionoethanephosphonic acid ester chloride, the batch was stirred for a further 12 hours and was washed twice with water, the organic layer was dried over sodium sulphate, the toluene was evaporated off under reduced pressure and the residue was distilled. 16 g (72% of theory) of O-methyl-O-(1-fluoro-2-chloro-ethyl)-thionoethanephosphonic acid ester of boiling point 48° C./0.01 mm Hg and refractive index $n_D^{22}$ of 1.4760 were obtained.

EXAMPLE 7

(a)
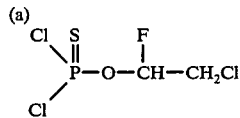

A mixture of 17 g of phosphorus sulphochloride and 12 g (0.05 mol) of O-(1-fluoro-2-chloro-ethyl)-phosphonic acid anhydride was heated for 15 hours to an external temperature of 150° C., cooled, diluted with 200 ml of ligroin, and filtered over kieselguhr. The solvent was evaporated off under reduced pressure and the residue was distilled. 7 g (61% of theory) of O-(1-fluoro-2-chloro-ethyl)-thionophosphoric acid ester dichloride, which according to a gas chromatogram was 90% pure and which had a boiling point of 65° C./3 mm Hg, were obtained.

(b)
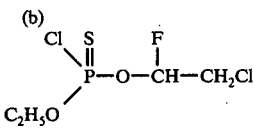

An 0.4 molar sodium ethylate solution was added dropwise, at 0° to 5° C., to a solution of O-(1-fluoro-2-chloro-ethyl)-thionophosphoric acid ester dichloride in 400 ml of toluene; the mixture was stirred for a further 10 minutes and was twice washed with water. The organic phase was dried over sodium sulphate and the toluene was distilled off under reduced pressure. The residue was distilled at 45° C./0.01 mm Hg. 75 g (78% of theory) of O-ethyl-O-(1-fluoro-2-chloro-ethyl)-thionophosphoric acid diester chloride were obtained.

(c)                                      (2)
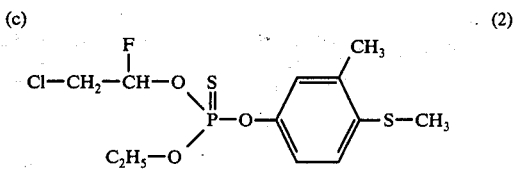

12 g (0.05 mol) of O-ethyl-O-(1-fluoro-2-chloro-ethyl)-thionophosphoric acid diester chloride were added all at once to a slurry of 100 ml of acetonitrile, 10 g (0.05 mol) of 3-methyl-4-methylthio-phenol and 10 g of potassium carbonate, in the course of which the internal temperature of the reaction mixture rose to 38° C. The batch was then stirred overnight, poured into water and extracted by shaking with methylene chloride, the organic phase was washed twice with water and dried over sodium sulphate, the methylene chloride was evaporated off under reduced pressure and the residue was subjected to slight distillation under greatly reduced pressure. 15 g (84% of theory) of O-ethyl-O-(1-fluoro-2-chloro-ethyl)-O-(3-methyl-4-methylthio-phenyl)-thionophosphoric acid ester having a refractive index $n_D^{23}$ of 1.5621 were obtained.

EXAMPLE 8

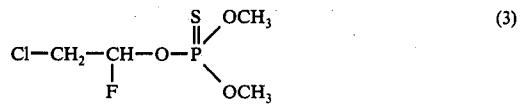
                                                 (3)

An 0.2 molar sodium methylate solution was added dropwise at 5° to 15° C. to a solution of 23 g (0.1 mol) of O-(1-fluoro-2-chloro-ethyl)-thionophosphoric acid ester dichloride in 200 ml of acetonitrile, the mixture was stirred for a further hour and the batch was poured into water and extracted by shaking with methylene chloride. The organic phase was washed twice with water and dried over sodium sulphate, and the solvent was removed under reduced pressure. The residue was distilled and 17 g (76% of theory) of O,O-dimethyl-O-(1-fluoro-2-chloro-ethyl)-thionophosphoric acid ester of boiling point 75°-80° C./4 mm Hg and refractive index $n_D^{25}$ of 1.5462 were thus obtained.

EXAMPLE 9

Another intermediate analogous to that produced in Example 7(b) was produced as follows:

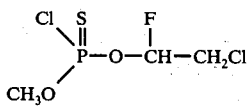

0.2 mol of a sodium methylate solution was added to a solution of 47 g (0.2 mol) of O-(1-fluoro-2-chloro-ethyl)-thionophosphoric acid ester dichloride in 300 ml of toluene, with external cooling. The mixture was stirred for a further 30 minutes at a temperature of up to 10° C. The batch was washed twich with water, the organic phase was dried over sodium sulphate, the toluene was evaporated off under reduced pressure and the residue was distilled. O-methyl-O-(1-fluoro-2-chloroethyl)-thionophosphoric acid diester chloride of boiling point 38°-42° C./0.01 mm Hg was obtained in 81% yield.

The following end products could be prepared in a manner analogous to those described in Examples 6 and 8:

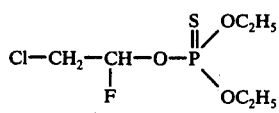 (4)

in 52% strength yield; refractive index $n_D^{22}$: 1.4543; boiling point 50° C./0.01 mm Hg

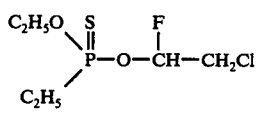 (5)

in 68% strength yield: refractive index $n_D^{22}$: 1.4700; boiling point 52° C./0.01 mm Hg

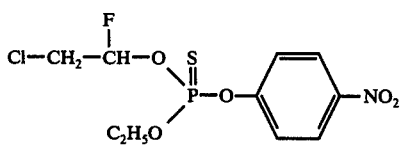 (6)

in 64% strength yield; refractive index $n_D^{23}$: 1.5382

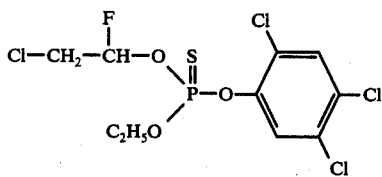 (7)

in 65% strength yield; refractive index $n_D^{22}$: 1.5474 as well as

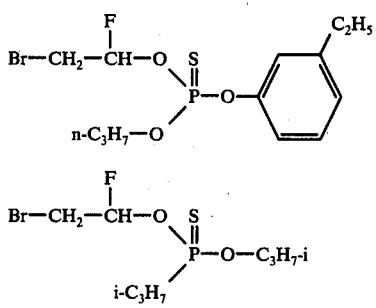

and the like.

It will be appreciated that the instant specification and examples are set forth by way of illustration and not limitation, and that various modifications and changes may be made without departing from the spirit and scope of the present invention.

What is claimed is:

1. An O-(1-fluoro-2-halogeno-ethyl)-thionophosphoric (phosphonic) acid ester of the formula

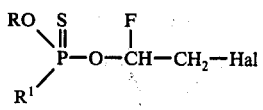

in which

R is alkyl, phenyl or phenyl carrying up to three substituents selected from the group consisting of halogen, alkyl, alkylthio and nitro, $R^1$ is alkyl or alkoxy, and Hal is halogen.

2. A method of combating arthropods or nematodes which comprises applying to the arthropods or nematodes, or to a habitat thereof, an arthropodicidal or nematicidally effective amount of a compound according to claim 1.

3. A compound according to claim 1 in which

R is alkyl with 1 to 3 carbon atoms, phenyl, chlorophenyl, nitrophenyl, alkylphenyl or alkyl-alkylthiophenyl with 1 to 3 carbon atoms per alkyl or alkylthio radical, $R^1$ is alkyl or alkoxy with 1 to 3 carbon atoms, and Hal is chlorine or bromine.

4. The compound according to claim 1 wherein such compound of O-methyl-O-(1-fluoro-2-chloro-ethyl)-thionoethane phosphonic acid ester of the formula

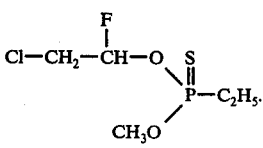

5. The compound according to claim 1 wherein such compound is O-ethyl-O-(1-fluoro-2-chloro-ethyl)-O-(3-methyl-4-methylthio-phenyl)-thionophosphoric acid ester of the formula

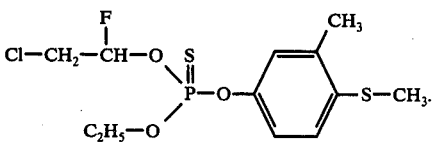

6. The compound according to claim 1 wherein such compound of O-ethyl-O-(1-fluoro-2-chloro-ethyl)-O-(4-nitrophenyl)-thionophosphoric acid ester of the formula

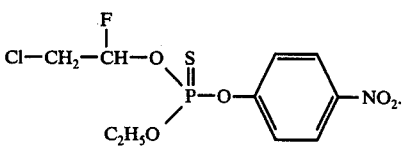

7. The compound according to claim 1 wherein such compound is O-ethyl-O-(1-fluoro-2-chloro-ethyl)-O-(2,4,5-trichlorophenyl)-thionophosphoric acid ester of the formula

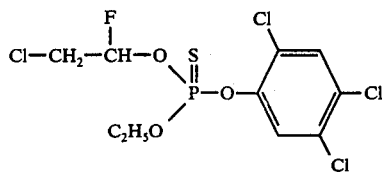

8. An arthropodicidal or nematicidal composition containing as active ingredient an arthropodicidal or nematicidally effective amount of a compound according to claim 1 in admixture with a diluent.

9. The method according to claim 2 in which said compound is
O-methyl-O-(1-fluoro-2-chloro-ethyl)-thionoethane phosphonic acid ester,
O-ethyl-O-(1-fluoro-2-chloro-ethyl)-O-(3-methyl-4-methylthio-phenyl)-thionophosphoric acid ester,
O-ethyl-O-(1-fluoro-2-chloro-ethyl)-O-(4-nitrophenyl)-thionophosphoric acid ester, or
O-ethyl-O-(1-fluoro-2-chloro-ethyl)-O-(2,4,5-trichloro-phenyl)-thionophosphoric acid ester.

* * * * *